(12) United States Patent
Jia et al.

(10) Patent No.: US 6,417,246 B1
(45) Date of Patent: Jul. 9, 2002

(54) DENTAL COMPOSITE MATERIALS

(75) Inventors: Weitao Jia; Shuhua Jin, both of Wallingford, CT (US)

(73) Assignee: Jenerica/Pentron Incorporated, Wallingford, CT (US)

( * ) Notice: Subject to any disclaimer, the term of this patent is extended or adjusted under 35 U.S.C. 154(b) by 7 days.

(21) Appl. No.: 09/660,111

(22) Filed: Sep. 12, 2000

Related U.S. Application Data

(60) Provisional application No. 60/155,292, filed on Sep. 21, 1999.

(51) Int. Cl.$^7$ .................................................. A61F 2/00
(52) U.S. Cl. ........................................ 523/113; 524/493
(58) Field of Search .......................................... 523/113

(56) References Cited

U.S. PATENT DOCUMENTS

| | | | |
|---|---|---|---|
| 3,066,112 A | | 11/1962 | Bowen |
| 3,179,623 A | | 4/1965 | Bowen |
| 3,194,784 A | | 7/1965 | Bowen |
| 3,751,399 A | | 8/1973 | Lee et al. |
| 3,926,906 A | | 12/1975 | Lee et al. |
| 4,491,508 A | * | 1/1985 | Olson .................... 204/159.13 |
| 4,544,359 A | | 10/1985 | Waknine |
| 4,547,531 A | | 10/1985 | Waknine |
| 4,649,165 A | * | 3/1987 | Kuhlman ..................... 523/116 |
| 4,885,332 A | * | 12/1989 | Bilkadi ....................... 524/714 |
| 5,126,394 A | * | 6/1992 | Revis .......................... 524/548 |
| 5,276,068 A | | 1/1994 | Waknine |
| 5,444,104 A | | 8/1995 | Waknine |
| 5,985,168 A | * | 11/1999 | Phule ....................... 252/62.52 |

\* cited by examiner

Primary Examiner—Paul R. Michl
(74) Attorney, Agent, or Firm—Cantor Colburn LLP

(57) ABSTRACT

A polymerizable dental composition, comprising a polymerizable resin composition; and a filler composition comprising a bound, nanostructured colloidal silica

12 Claims, No Drawings

DENTAL COMPOSITE MATERIALS

CROSS-REFERENCE TO RELATED APPLICATIONS

This application claims priority to provisional application Ser. No. 60/155,292, filed Sep. 21, 1999, which is incorporated by reference herein in its entirety.

BACKGROUND OF THE INVENTION

1. Field of the Invention

This invention relates to composite materials for restorative dentistry. More particularly, it relates to composites which are useful as crown and bridge materials, either with or without an alloy substrate; as reconstructive materials, restorative materials, filling materials, inlays, onlays, laminate veneers, dental adhesives, cements, sealants and the like.

2. Brief Description of the Related Art

In recent years, materials used for dental restorations have comprised principally acrylate or methacrylate polymers. Typical acrylate resinous materials are disclosed in U.S. Pat. No. 3,066,112 to Bowen, U.S. Pat. No. 3,179,623 to Bowen, U.S. No. 3,194,784 to Bowen, U.S. Pat. No. 3,751,399 to Lee et al. and U.S. Pat. No. 3,926,906 to Lee et al. An especially important methacrylate monomer is the condensation product of bisphenol A and glycidyl methacrylate, 2,2'-bis[4-(3-methacryloxy-2-hydroxy propoxy)-phenyl]-propane (hereinafter abbreviated "Bis-GMA"). Polyurethane dimethacrylates (hereinafter abbreviated to PUDMA) are also commonly used principal polymers in dental restorative materials of this type. Since Bis-GMA is highly viscous at room temperature, it is generally diluted with an acrylate or methacrylate monomer having a lower viscosity such as trimethylol propyl trimethacrylate, 1,6-hexanediol dimethacrylate, 1,3-butanediol dimethacrylate, and the like. Other dimethacrylate monomers, such as ethylene glycol dimethacrylate, diethylene glycol dimethacrylate, triethylene glycol dimethacrylate, and tetraethylene glycol dimethacrylate, are also in general use as diluents.

Because acrylic materials exhibit high coefficients of thermal expansion relative to the coefficient of thermal expansion for the tooth structure, these substances by themselves proved to be less than satisfactory. The disparity in thermal expansion, coupled with high shrinkage upon polymerization, resulted in poor marginal adaptability and ultimately led to secondary decay. Furthermore, the wear and abrasion characteristics and the overall physical, mechanical, and optical properties of these unfilled acrylic resinous materials were quite poor. Composite dental restorative materials containing methacrylate resins and fillers were thus developed, the fillers generally comprising inorganic materials based on silica, silicate glass, or quartz. Particularly suitable improved inorganic filler materials include those disclosed in commonly assigned U.S. Pat. No. 4,547,531 to Waknine, and U.S. Pat. No. 4,544,359 to Waknine. Despite their suitability for their intended purposes, there nevertheless remains a perceived need in the art for dental resin materials with even more advantageous physical properties.

SUMMARY OF THE INVENTION

The drawbacks and deficiencies of the prior art are remedied by a dental composite comprising a resin composition and a filler composition, wherein the filler composition comprises a nanostructured, bound silica. Preferably, the bound silica comprises colloidal, nanosized particles having their largest dimensions in the range from about 10 to about 50 nanometers (nm). The silica particles are preferably bound in the form of chains having lengths in the range from about 50 nm to about 400 nm.

These filled compositions are useful for a variety of dental treatments and restorative functions including crown and bridge materials, fillings, adhesives, sealants, luting agents or cements, denture base materials, orthodontic materials and sealants, and other dental restorative materials.

Detailed Description of the Preferred Embodiments

The present dental composite comprises a resin composition and a filler composition, wherein the filler composition comprises a nanostructured, bound silica, preferably in the form of nanosized particles having their largest dimensions in the range from about 10 to about 50 nanometers (nm). silica particles are preferably bound so as to result in chains having lengths in the range from about 50 nm to about 400 nm. Also within the scope of the invention described herein are methods for use of the preceding materials. Resin Composition Resin compositions are well known in the art, generally comprising viscous acrylate or methacrylate monomers such as those disclosed in U.S. Pat. No. 3,066,112 to Bowen, U.S. Pat. No. 3,179,623 to Bowen, U.S. Pat. No. 3,194,784 to Bowen, No. 3,751,399 to Lee et al., U.S. Pat. No. 3,926,906 to Lee et al., and commonly assigned U.S. Pat. Nos. 5,276,068 and Pat. No. 5,444,104 to Waknine, all of which are incorporated herein by reference. Other resin materials include, but are not limited to, urethane dimethacrylate (UDMA), diurethane dimethacrylate (DUDMA), and other monomers and oligomers known in the art. A useful oligomer is disclosed in U.S. Pat. Nos. 5,276,068 and U.S Pat. No. 5,444,104 to Waknine, being a polycarbonate dimethacrylate (PCDMA) which is the condensation product of two parts of a hydroxyalkylmethacrylate and 1 part of a bis(chloroformate). Another advantageous resin having lower water sorption characteristics is an ethoxylated bisphenol A dimethacrylate (EBPDMA) as disclosed in U.S. Pat. No. 6,013,694. Included within the scope of the resin compositions herein are the resin compositions suitable for use with glass ionomer cements, including polycarboxylic acids such as homo- and copolymers of acrylic acid and/or itaconic acid.

In addition to the aforementioned monomers and oligomers, the resin compositions can further include a diluent acrylate or methacrylate monomer to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate and tetra(ethylene glycol) dimethacrylate; and diol dimethacrylates such as butanedimethacrylate, dodecanedimethacryalte, or 1,6-hexanedioldimethacrylate. Tri(ethylene glycol) dimethacrylate (TEGDMA) is particularly preferred.

The more viscous monomers, i.e., UDMA, Bis-GMA, and the like are generally present in an amount in the range from 30 to about 100 percent by weight of the total resin composition, preferably in an amount in the range from about 50 to about 90 percent by weight of the total resin composition, and even more preferably in an amount from about 50 to about 80 percent by weight of the total resin composition. Diluent monomers, when present, are incorporated into the resin composition in an amount from about 1 to about 70 weight percent of the total resin composition.

In addition to the above monomers and oligomers, the resin compositions also typically include polymerization initiators, polymerization accelerators, ultraviolet light absorbers, antioxidants, and other additives well known in the art.

Suitable polymerization initiators are those conventional initiators known in the art. For example, visible light curable compositions employ light-sensitive compounds such as benzil diketones, and in particular, DL-camphorquinone in amounts ranging from about 0.05 to 0.5 weight percent. Self-curing compositions will generally contain free radical polymerization initiators such as, for example, a peroxide in amounts ranging from about 2 to 6 weight percent. Particularly suitable free radical initiators are lauryl peroxide, tributyl hydroperoxide and, more particularly, benzoyl peroxide.

Polymerization accelerators suitable for use are the various organic tertiary amines well known in the art. In visible light curable compositions, the tertiary amines are generally acrylate derivatives such as dimethylaminoethyl methacrylate and, particularly, diethylaminoethyl methacrylate (DEAEMA) in amounts ranging from about 0.05 to 0.5 weight percent. In the self-curing compositions, the tertiary amines are generally aromatic tertiary amines, such as dimethyl-p-toluidine, dihydroxyethyl-ptoluidine and the like, in amounts ranging from about 0.05 to about 4.0 weight percent.

It is furthermore preferred to employ an ultraviolet absorber in amounts ranging from about 0.05 to about 5.0 weight percent. Such UV absorbers are particularly desirable in the visible light curable compositions in order to avoid discoloration of the resin from any incident ultraviolet light. Suitable UV absorbers are the various benzophenones, particularly UV_5411 available from American Cyanamid Company.

Filler Composition

The filler composition comprises at least a bound, nanostructured, silica. The silica is in the form of nanosized particles, preferably spherical particles. The individual particles have a largest dimension or diameter in the range from about 10 to about 100 nm and preferably from about 10 to about 50 nm. The silica particles are furthermore bound to each other so as to result in chains having lengths in the range from about 50 nm to about 400 nm. Such silica is commercially available as a colloidal silica sol in water from Nissan Chemical Industries, Ltd. under the trade name SNOWTEX-PS™, and from Nissan Chemical Company, under the trade name MA-ST-UP. Without being bound by theory, it is hypothesized that the "strings" of bound silica improve fracture resistance compared to discrete, particulate materials. In order to improve bonding with the resin matrix, the bound colloidal silica filler particles may optionally be treated with a silane, for example gamma-mercaptopropyltrimethoxysilane, gamma-mercaptopropyltriethoxysilane, gamma-aminopropyltriethoxysilane, and the like.

In addition to the bound, nanostructured silica, the filler composition may further comprise one or more of the inorganic fillers currently used in dental restorative materials. Preferred additional fillers include those which are capable of being covalently bonded to the resin matrix itself or to a coupling agent which is covalently bonded to both. Examples of suitable filling materials include but are not limited to, silica, silicate glass, quartz, barium silicate, strontium silicate, barium borosilicate, strontium borosilicate, borosilicate, lithium silicate, lithium alumina silicate, amorphous silica, ammoniated or deammoniated calcium phosphate and alumina, zirconia, tin oxide, and titania. Suitable fillers have a particle size in the range from about 0.1–5.0 microns, and may further comprise unbound silicate colloids of about 0.001 to about 0.07 microns. These additional fillers may also be silanized. Some of the aforementioned inorganic filling materials and methods of preparation thereof are disclosed in U.S. Pat. Nos. 4,544,359 and No. 4,547,531, pertinent portions of which are incorporated herein by reference. Fillers suitable for use with glass ionomer cements are ion leachable glasses such as finely ground silica, silicate glass, fluorosilicate, fluoroborosilicate, calcium silicate, calcium alumino silicate, aluminosilicate, calcium aluminum fluorosilicate glass, and mixtures thereof.

The amount of total filler composition in the dental composite can vary widely, being in the range from about 1 to about 90 percent by weight (wt. %) of the total composition. The amount used is determined by the requirements of the particular application. Thus, for example, crown and bridge materials generally comprise from about 60 to about 90 wt. % filler; luting cements comprise from about 20 to about 80 wt. % filler; sealants generally comprise from about 1 to about 20 wt. % filler; adhesives generally comprise from about 1 to about 30 wt. % filler; and restorative materials comprise from about 50 to about 90% filler, with the remainder in all cases being the resin composition.

The amount of bound, nanostructured colloidal silica in the dental composition relative to other filler may also vary widely, depending on the requirements of the particular application. The bound, nanostructured colloidal silica may accordingly comprise from less than 1 to 100 wt. % of the total filler composition, preferably from 1 to 100 wt. % for sealers and adhesives, and from about 2 to about 30 wt. % for crown and bridge materials and dental restorative materials.

Methods for use of the above-described compositions are well known in the art. For example, a site to be restored in a tooth is prepared, and the above-described composition is applied to the site.

The invention is further illustrated by the following non-limiting examples. Examples.

A base resin mixture was prepared, comprising EBPDMA and PCDMA in a ratio of 70/30 by weight, and further comprising 0.2 wt. % of camphorquinone and 0.4 wt. % of DEAEMA. Elongated, bound colloidal silica in the form of 20 wt % methanol solution (available under the trade name MA-ST-UP, from Nissan Chemical, Houston, Tex.) was blended with the above base resin mixture so as to provide from 0 to 20 wt. % of the silica. Some silica was silanated by treatment with 10 wt. % gamma-(methacryloyloxy) propyltrimethoxy silane (Aldrich, Milwaukee, Wis.) based on the toal amount of silica. After stirring with the silica/bas resin mixture for an hour, the methanol was removed under vacuum. A control was also prepared, comprising regular colloidal silica in isopropanol (Hinklink OG 502-31, commercially available from Clariant, Charlotte, N.C.) blended into the same resin mix in an amount of 10 wt. % of silica.

Flexural strength and surface Barcol Hardness were measured after polymerization. Flexural strength was measured on 2×2×25 mm bars prepared and tested according to ADA Specification No.27. Hardness was measured on disks 10 mm in diameter and 3 mm in thickness and cured for two minutes inside a CureLite Plus (Jeneric/Pentron, Inc., Wallingford, Conn.) curing unit. A Barcol Hardness Impressor (Barber-Colman Company, Ill.) was used to measure the surface hardness and recorded as Barcol Hardness number. Results are shown in the Table below:

| No. | Silica (Wt. %) | Silane treatment | Flexural Strength (psi) | Barcol Hardness |
|---|---|---|---|---|
| 1* | 0 | — | 11133 | 77 |
| 2 | 2 | no | 11631 | 79 |
| 3 | 10 | no | 12598 | 80 |
| 4 | 2 | yes | 11465 | 78 |
| 5 | 5 | yes | 13319 | 78 |
| 6 | 10 | yes | 13196 | 85 |
| 7 | 20 | yes | 14910 | 90 |
| 8** | 10 | no | 6159 | 80 |

*Control: Unfilled resin only
**Control: Resin filled with 10% by wt. SiO$_2$ of Hinklink OG 502-31 (Clariant, Charlotte, NC)

As may be seen by reference to the above data, use of elongated colloidal silica is an improvement over unfilled resin. Surprisingly, it also performs much better than the spherical colloidal silica. The higher the quantity of elongated silica incorporated into the resin matrix, the better the strength and hardness. A precipitated phase of the silica may occur if the silica amount is above about 15% in the untreated case and about 25% in the silane treated compositions.

While preferred embodiments have been shown and described, various modifications and substitutions may be made thereto without departing form the spirit and scope of the invention. Accordingly, it is to be understood that the present invention has been described by way of illustration and not limitation.

What is claimed is:

1. A polymerizable dental composition, comprising
    a polymerizable resin composition; and
    a filler composition comprising manostructured colloidal silica particles, wherein the silica particles are bound to each other to form chains.

2. The composition of claim 2, wherein the silica is in the form of particles having their largest dimensions in the range from about 10 to about 50 nanometers.

3. The composition of claim 1, wherein the silica particles are bound in the form of chains having lengths in the range from about 50 nm to about 400 nm.

4. The composition of claim 1, wherein the silica particles are spherical.

5. A dental restoration comprising
    a polymerizable resin composition; and
    a filler composition comprising nanostructured colloidal silica particles, wherein the silica particles are bound to each other to form chains.

6. The restoration of claim 5, wherein the silica is in the form of particles having their largest dimensions in the range from about 10 to about 50 nanometers.

7. The restoration of claim 5, wherein the silica particles are bound in the form of chains having lengths in the range from about 50 nm to about 400 nm.

8. The restoration of claim 5, wherein the silica particles are spherical.

9. A method of making a dental restoration, comprising
    preparing a site to be restored; and
    applying a polymerizable dental composition comprising a polymerizable resin composition and a filler composition comprising nanostructured colloidal silica particles, wherein the silica particles are bound to each other to form chains.

10. The method of claim 9, wherein the silica is in the form of particles having their largest dimensions in the range from about 10 to about 50 nanometers.

11. The method of claim 9, wherein the silica particles are bound in the form of chains having lengths in the range from about 50 mn to about 400 nm.

12. The method of claim 9, wherein the silica particles are spherical.

* * * * *

UNITED STATES PATENT AND TRADEMARK OFFICE
CERTIFICATE OF CORRECTION

PATENT NO. : 6,417,246 B1
DATED : July 9, 2002
INVENTOR(S) : Weitao Jia et al.

It is certified that error appears in the above-identified patent and that said Letters Patent is hereby corrected as shown below:

Column 1,
Line 24, after "U.S." (first occurrence) insert -- Pat. --.

Column 2,
Line 23, after "materials." delete "Resin Composition" and insert on line 24.

Column 3,
Line 29, after "dimethyl-p-toluidine" delete "dihydroxyethyl-ptoluidine" and insert -- dihydroxyethyl-p-toluidine --.

Column 4,
Line 45, after "examples." delete "Examples." and insert on line 46.

Column 5,
Line 38, after "comprising" delete "manostructured" and insert -- nanostructured --.

Signed and Sealed this

Thirty-first Day of January, 2006

JON W. DUDAS
*Director of the United States Patent and Trademark Office*